United States Patent
Koh et al.

(10) Patent No.: US 7,363,086 B1
(45) Date of Patent: Apr. 22, 2008

(54) CAPTURE VERIFICATION IN RESPIRATORY DIAPHRAGM STIMULATION

(75) Inventors: Steve Koh, South Pasadena, CA (US); Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 222 days.

(21) Appl. No.: 11/086,613

(22) Filed: Mar. 21, 2005

(51) Int. Cl.
*A61N 1/36* (2006.01)

(52) U.S. Cl. .......................... 607/42; 607/118

(58) Field of Classification Search .............. 607/6, 607/17, 18, 20, 42
See application file for complete search history.

(56) References Cited

U.S. PATENT DOCUMENTS

| | | | |
|---|---|---|---|
| 4,686,988 A | 8/1987 | Sholder | 128/419 PT |
| 4,712,555 A | 12/1987 | Thornander et al. | 128/419 PT |
| 4,788,980 A | 12/1988 | Mann et al. | 128/419 PG |
| 4,827,935 A * | 5/1989 | Geddes et al. | 607/42 |
| 4,940,052 A | 7/1990 | Mann et al. | 128/419 PG |
| 4,944,298 A | 7/1990 | Sholder | 128/419 PG |
| 5,466,254 A | 11/1995 | Helland | 607/123 |
| 5,573,550 A | 11/1996 | Zadeh et al. | 607/28 |
| 6,314,323 B1 | 11/2001 | Ekwall | 607/23 |
| 6,415,183 B1 * | 7/2002 | Scheiner et al. | 607/42 |
| 6,463,327 B1 | 10/2002 | Lurie | 607/42 |
| 6,587,726 B2 | 7/2003 | Lurie et al. | 607/42 |
| 2003/0195571 A1 | 10/2003 | Burnes et al. | 607/9 |

FOREIGN PATENT DOCUMENTS

WO   WO 03/086531 A2   10/2003

* cited by examiner

*Primary Examiner*—Carl Layno
*Assistant Examiner*—Brian T Gedeon

(57) ABSTRACT

Improved methods and devices perform respiratory control of a person due to conditions such as sleep apnea. According to one embodiment, a respiratory control method includes delivering stimulation signals according to one or more stimulation parameters to phrenic nerves of a person. The person's chest activity is monitored, e.g., by sensing signals in a chamber of the person's heart, to determine the person's respiratory cycle. The stimulation cycle and respiratory cycle are compared. In response, the one or more stimulation parameters are adjusted. In subsequent stimulation cycle(s), the method delivers the stimulation signals according to the adjusted stimulation parameters. This feedback mechanism may continue until respiratory control is captured.

15 Claims, 7 Drawing Sheets

US 7,363,086 B1

CAPTURE VERIFICATION IN RESPIRATORY DIAPHRAGM STIMULATION

FIELD OF THE INVENTION

The present invention relates generally to implantable therapy devices and, more particularly, to devices for treatment of apnea.

BACKGROUND

Millions of people are affected by sleep apnea, a condition in which a person's breathing is interrupted, often repeatedly, during their sleep due to the person's airway becoming blocked. Sleep apnea can cause chocking spells, fatigue, mood swings, and more serious conditions. Fortunately, sleep apnea is a treatable condition.

Breathing is controlled by a pair of nerves called the "phrenic nerves" which are located in the neck, at the base of the brain, and extend down to the diaphragm. The phrenic nerves carry the stimuli from the brain to the diaphragm, the primary muscle used in breathing. When a person breathes in, the diaphragm moves down and air moves into the lungs. This is called inspiration. When the person breathes out, air moves out of the lungs. This is called expiration. When no stimuli are present in the phrenic nerves, the diaphragm does not contract to create more air space. As a result, the person's breathing is interrupted.

Implantable stimulation devices have been proposed to treat people who suffer from sleep apnea. These devices send stimulation pulses to the phrenic nerves to control the diaphragm and thus the person's breathing. Timing of such stimulation pulses is critical as any incorrect or untimely stimulation pulses may alarm/surprise the person. Moreover, closely spaced respiration may not be effective in air movement. Specifically, untimely and/or incorrect stimulation signals can wake up the sleeping person, thus compromising the person's already unstable sleeping session due to sleep apnea.

BRIEF SUMMARY

In one embodiment, a method comprises delivering stimulation according to one or more stimulation parameters to cause contraction of the diaphragm, and monitoring chest activity related to respiration. The method further comprises comparing a stimulation interval and a sensed respiration interval, and, in response, adjusting one or more of the one or more stimulation parameters and delivering adjusted stimulation based on the one or more adjusted parameters.

DETAILED DESCRIPTION

Figure 1:
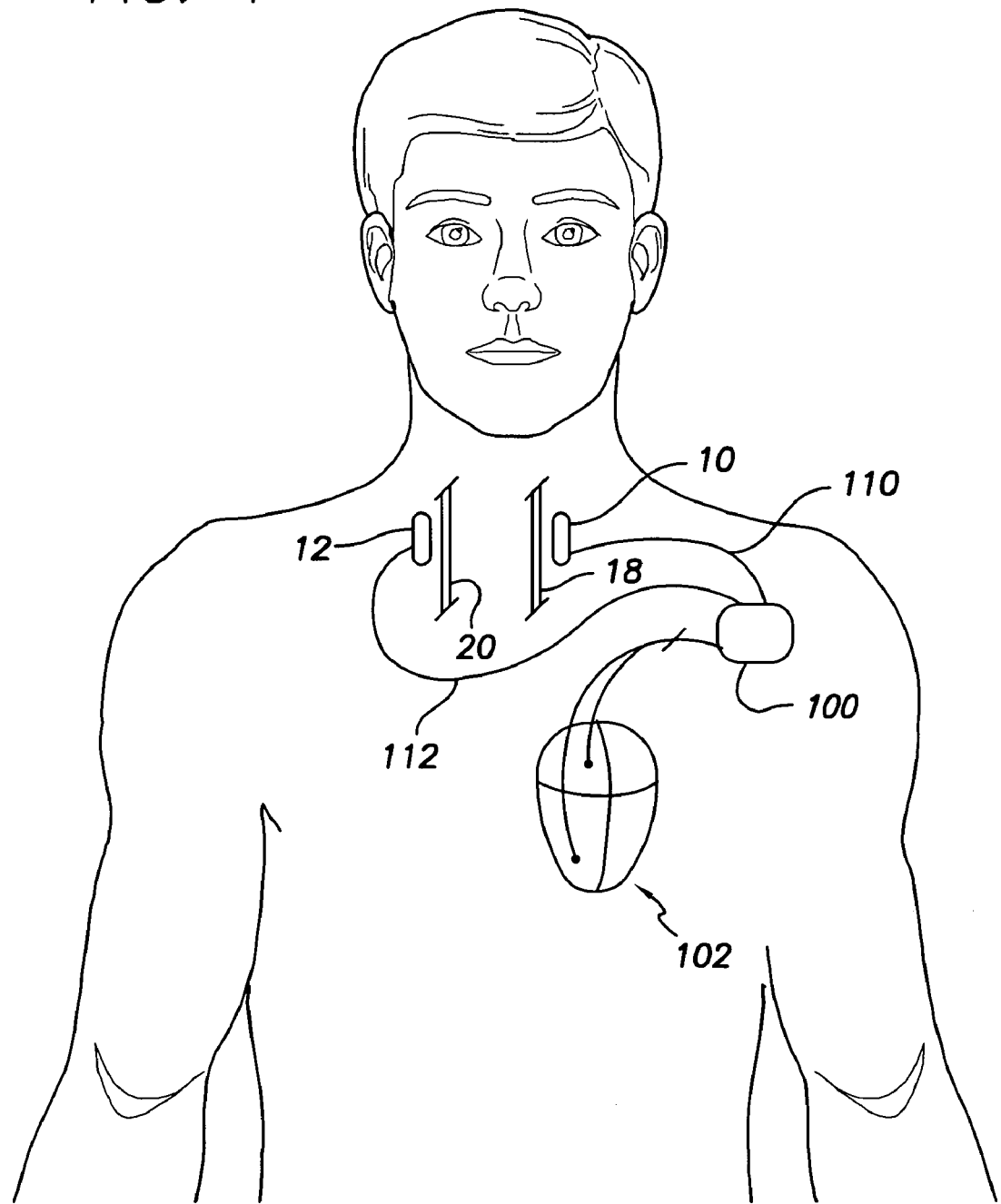
FIG. 1 illustrates a diagram of a person with an implantable device in communication with leads and/or sensors implanted in a person body.

FIG. 1 is a diagram of a person in which a device 100 is implanted in his body. The implantable therapy or monitoring device 100 is used to treat sleep apnea and other conditions, such as tachycardia. Also implanted in the person's body are phrenic nerve stimulators 10 and 12 positioned near the person's phrenic nerves 18 and 20, respectively. The device 100 is in communication with the phrenic nerve stimulators 10 and 12 via leads 110 and 112, respectively, for sensing the presence of stimuli and/or delivering stimuli to the phrenic nerves 18 and 20 to help the person breathe (e.g., in response to detection of sleep apnea), according to one or more embodiments disclosed herein. The device 100 is also in communication with leads implanted in one or more chambers located in a patient's heart 102, such as the left ventricle, left atrial, right ventricle, and/or right atrial (only two leads are shown). In one or more embodiments disclosed herein, the device 100 senses signals located in one or more chambers of the heart 102 to measure the impedance and impedance cycle length in order to determine the person's respiration.

Figure 2:
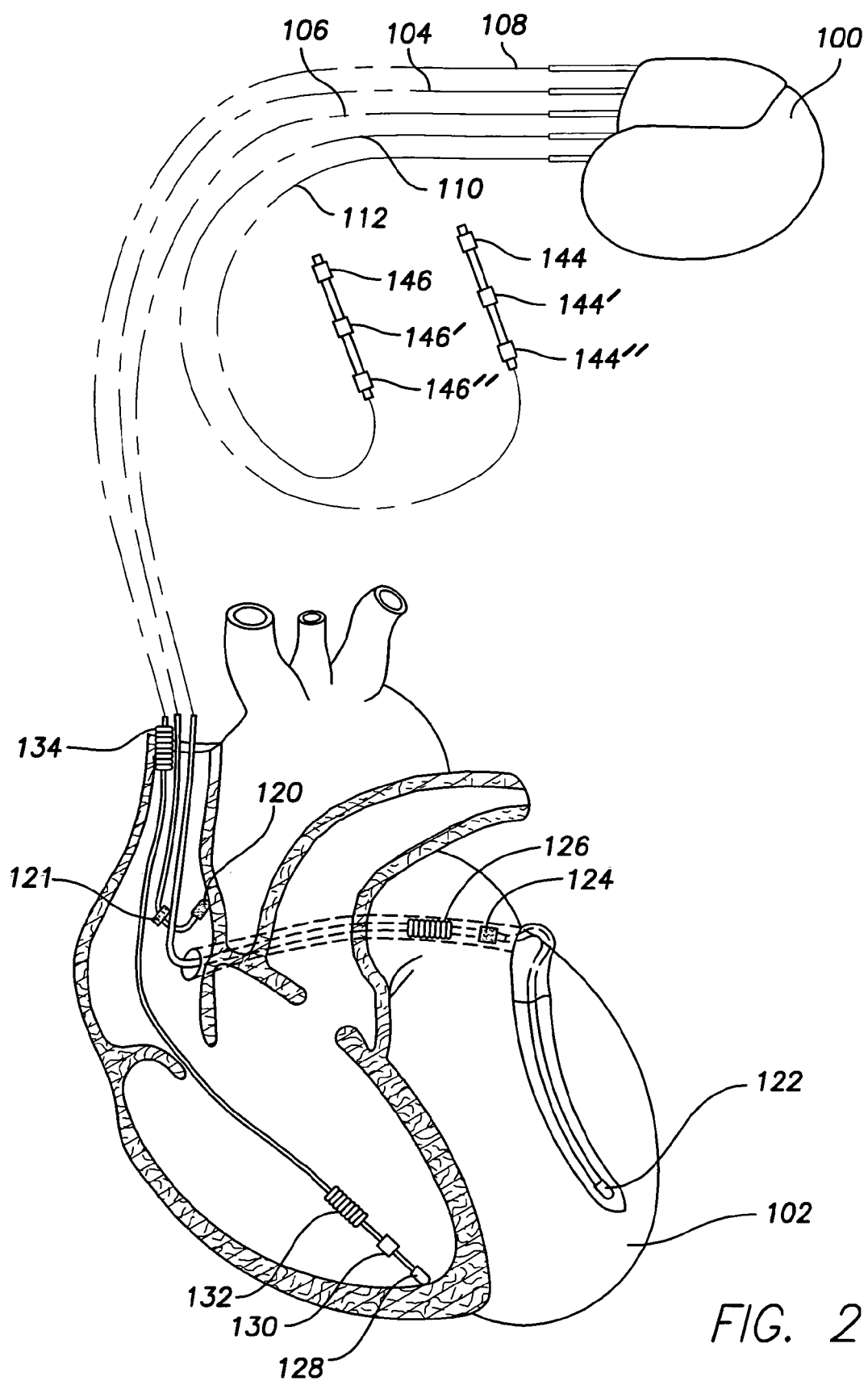
FIG. 2 is a simplified diagram illustrating an exemplary implantable device in electrical communication with a plurality of leads implanted into a patient's heart and other parts of the body for sensing signals and delivering stimulation.

As shown in FIG. 2, there is an exemplary device 100 in electrical communication with a patient's heart 102 by way of three leads 104, 106, and 108, suitable for sensing cardiac signals in one or more chambers of the heart 102, and delivering multi-chamber stimulation and shock therapy. The leads 104, 106, 108 are optionally configurable for delivery of stimulation pulses suitable for stimulation of nerves (e.g., autonomic nerves, phrenic nerves, etc.) and/or muscle tissue other than myocardial tissue. In addition, fourth and fifth leads 110 and 112 are coupled to device 100. Leads 110 and 112 each includes three electrodes 144, 144', 144" (and 146, 146', and 146") which are positioned next to the phrenic nerves 18 and 20, suitable for stimulation of the phrenic nerves and sensing of the presence of intrinsic stimuli in the phrenic nerves 18 and 20. Each of leads 110 and 112 may include more or less electrodes.

The right atrial lead 104 is positioned in and/or passes through a patient's right atrium. The right atrial lead 104 is configurable to sense atrial cardiac signals and provide right atrial chamber stimulation therapy. As shown in FIG. 2, the device 100 is coupled to the implantable right atrial lead 104 having, for example, an atrial tip electrode 120, which typically is implanted in the patient's right atrial appendage. The lead 104 also includes an atrial ring electrode 121. The lead 104 may have other electrodes as well. For example, the right atrial lead optionally includes a distal bifurcation having electrodes suitable for sensing cardiac signals and stimulation of nerves and/or muscle tissue.

To sense left atrial and ventricular cardiac signals and to provide left chamber pacing therapy, the device 100 is coupled to a "coronary sinus" lead 106 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is configurable to receive/sense atrial and ventricular cardiac signals and to deliver left atrial and ventricular pacing therapy using at least a left ventricular (LV) tip electrode 122, a left atrial ring electrode 124, and/or a left atrial coil electrode 126. At least the left atrial coil electrode 126 may be used to delivery shocking therapy. For a description of an exemplary coronary sinus lead, see U.S. Pat. No. 5,466,254, "Coronary Sinus Lead with Atrial Sensing Capability" (Helland), which patent document is incorporated herein by reference. Coronary sinus lead 106 can also include additional electrodes that may be used to sense and/or provide pacing therapy in the atrial and/or ventricular chambers.

The device 100 is also shown in electrical communication with the patient's heart 102 by way of an implantable right ventricular lead 108 having, in this embodiment, an RV tip electrode 128, an RV ring electrode 130, an RV coil electrode 132, and a superior vena cava (SVC) coil electrode 134 (also known as a right atrial (RA) coil electrode). Typically, the right ventricular lead 108 is transvenously inserted into the heart 102 so as to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving/sensing cardiac signals for measuring intrathoracic impedance using one or more of the aforementioned electrodes. The right ventricular lead 108 is also capable of delivering stimulation to one or more of the electrodes in the form of pacing and shock therapy to the right ventricle.

Figure 3:
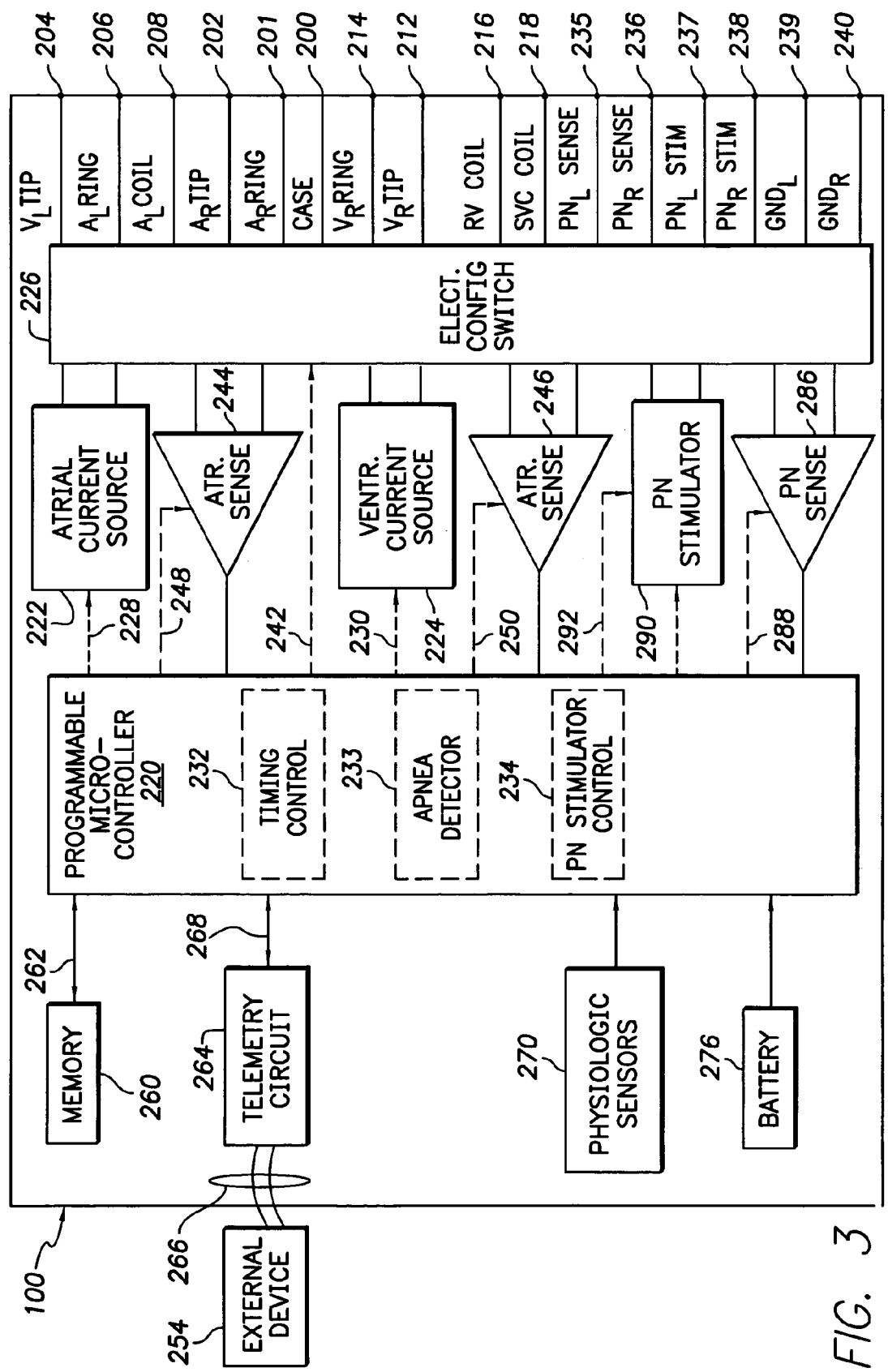
FIG. 3 is a functional block diagram of the implantable device of FIG. 2 illustrating the basic elements of the device.

FIG. 3 shows an exemplary, simplified block diagram depicting various components of the device 100. In one or more embodiments, the device 100 detects the presence of sleep apnea, and, in response, delivers stimuli to one or both phrenic nerves (and/or other nerves such as autonomic nerves, etc.), and continually senses cardiac signals in one or more chambers of the heart 102 and adjusts stimuli to the phrenic nerves, in order to capture respiratory contraction. The device 100 is also capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device.

The housing 200 for the device 100 is often referred to as the "can", "case" or "case electrode" and may be programmably selected to act as the return electrode for all "unipolar" modes. The housing 200 may further be used as a return electrode alone or in combination with one or more of the coil electrodes 126, 132, and 134 for shocking purposes. The housing 200 further includes a connector (not shown) having a plurality of terminals 201, 202, 204, 206, 208, 212, 214, 216, 218, and 235-240 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

To achieve left and right phrenic nerve sensing, the connector includes left and right phrenic nerve sensing terminals 235 ($PN_L$ SENSE) and 236 ($PN_R$ SENSE). The terminals 235 and 236 are adapted for connection to sensing electrodes 144 and 146, respectively. To achieve left and right phrenic nerve stimulation, the connector includes left and right phrenic nerve stimulation terminals 237 ($PN_L$ STIM) and 238 ($PN_R$ STIM). The terminals 237 and 238 are adapted for connection to stimulation electrodes 144' and 146', respectively. The connector also includes ground terminals 239 and 240 adapted for connection to electrodes 144" and 146", respectively. These terminals are used as the return path for phrenic nerve sensing and stimulation.

At the core of the device 100 is a programmable microcontroller 220 which controls the various modes of sensing and stimulation therapy, particularly detection and treatment of sleep apnea. As is well known in the art, the microcontroller 220 typically includes a microprocessor, or equivalent control circuitry, designed specifically for controlling the sensing of signals and delivery of stimulation therapy, and may further include RAM or ROM memory, logic and timing circuitry, state machine circuitry, and I/O circuitry. Typically, the microcontroller 220 includes the ability to process or monitor input signals (data) as controlled by a program code stored in a designated block of memory. Any suitable microcontroller, microprocessor, or other CPU 220 may be used that carries out the functions described herein. The use of microprocessor-based control circuits for performing timing and data analysis functions are well known in the art.

Representative types of control circuitry that may be used herein include the microprocessor-based control system of U.S. Pat. No. 4,940,052 (Mann et. al.) and the state-machines of U.S. Pat. Nos. 4,712,555 (Thornander et al.) and 4,944,298 (Sholder). For a more detailed description of the various timing intervals used within the device and their inter-relationship, see U.S. Pat. No. 4,788,980 (Mann et. al.). The '052, '555, '298 and '980 patents are incorporated herein by reference.

The device 100 includes atrial sensing circuits 244 and ventricular sensing circuits 246, which are selectively coupled to one or more of the right atrial lead 104, coronary sinus lead 106, and the right ventricular lead 108, through an electrode configuration switch 226 (also referred to as switch bank 226) for detecting the presence of cardiac activity in each of the four chambers of the heart. The atrial (ATR. SENSE) and ventricular (VTR. SENSE) sensing circuits 244 and 246, may include dedicated sense amplifiers, multiplexed amplifiers, or shared amplifiers. Each circuit 244 and 246 (and 286) is configurable to perform D/A conversion of sensed signals. The switch 226 determines the "sensing polarity" of the cardiac signal by selectively closing the appropriate switches, as is known in the art. In this way, the clinician may program the sensing polarity independent of the stimulation polarity. The sensing circuits 244 and 246 are controlled by the microcontroller 220 via signal lines 248 and 250, respectively, for purposes of controlling the gain, threshold, the polarization charge removal circuitry (not shown), and the timing of any blocking circuitry (not shown) coupled to the inputs of the sensing circuits 244 and 246 as is known in the art. The sensing circuits 244, 246, via switches, etc., are configurable to sense information related to respiration (e.g., chest movement monitoring, etc.) including the voltage level in one or more chambers of the heart, as described further below.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation. For a complete description of a typical sensing circuit, see U.S. Pat. No. 5,573,550, entitled "Implantable Stimulation Device having a Low Noise, Low Power, Precision Amplifier for Amplifying Cardiac Signals" (Zadeh et al.), which is incorporated herein by reference.

Continuing to refer to FIG. 3, an atrial current source 222 and a ventricular current source 224 generate current for delivery by the right atrial lead 104, the right ventricular lead 108, and/or the coronary sinus lead 106 via switch 226. The operation of the current sources 222 and 224 will be described in more detail below. The microcontroller 220 is capable of independently triggering or inhibiting the atrial and ventricular current sources 222 and 224 via appropriate control signals 228 and 230, respectively, in a demand fashion in the appropriate chambers of the heart.

The device 100 further includes a phrenic nerve (PN) sensing circuit 286 and PN stimulator 290. PN sensing circuit 286 is selectively coupled to the left and right phrenic nerve sensing and ground terminals 235, 239 ($PN_L$ SENSE) and 236, 240 ($PN_R$ SENSE) through switch 226 for detecting the presence of stimuli in the left and right phrenic nerves 18 and 20 via sensing electrodes 144, 144" and 146, 146", respectively. It should be noted that a dedicated PN sensing circuit may be used for each phrenic nerve or a single, shared or multiplexed PN sensing circuit can be used to sense stimuli at both phrenic nerves 18 and 20. Accordingly, the PN sensing circuit 286 may include dedicated sense amplifiers, multiplexed amplifiers, or shared amplifiers. The switch 226 determines the "sensing polarity" of the cardiac signal by selectively closing the appropriate switches, as is known in the art. In this way, the clinician may program the sensing polarity independent of the stimulation polarity. The PN sensing circuit 286 via switches, etc., may also be used to sense information related to respiration (e.g., chest movement monitoring, etc.) from the person's heart. The phrenic nerve (PN) stimulator 290 generates stimulation pulses for delivery by the one or both phrenic nerve leads 237, 239 and 238, 240 via switch 226 to respective stimulation electrodes 144', 144" and 146', 136", respectively. It is understood that in order to provide stimulation to the left and right phrenic nerves, the PN stimulator 290 may include dedicated, independent stimulators, multiplexed stimulators, or shared stimulators. For sake of brevity, the description that follows refers only to a single stimulator 290. The PN sensing circuit 286 and PN stimulator 290 are controlled by the microcontroller 220 via appropriate control signal line(s) 288 and 292, respectively, to trigger or inhibit sensing and stimulation signals or pulses. In one or more embodiments, phrenic nerve signals are sensed and phrenic nerve stimulation pulses are delivered in a unipolar or bipolar fashion.

The microcontroller 220 also includes timing control circuitry 232 which is used to control the timing of sensed as well as stimulation signals. Microcontroller 220 further includes an apnea detector module 233 and PN stimulator control module 234. Apnea detector 233 is utilized to determine the presence of (sleep) apnea and PN stimulator control module 234 is utilized to treat apnea, as will be described in more detail below. These components may be implemented in hardware as part of the microcontroller 220, or as software/firmware instructions programmed into the device and executed on the microcontroller 220 during certain modes of operation. Various exemplary methods described herein are optionally implemented as logic, which may be embodied in software and/or hardware.

The electronic configuration switch 226 includes a plurality of switches for connecting the desired electrodes to the appropriate I/O circuits, thereby providing complete electrode programmability. Accordingly, the switch 226, in response to a control signal 242 from the microcontroller 220, determines the polarity of the stimulation pulses (e.g., unipolar, bipolar, combipolar, etc.) by selectively closing the appropriate combination of switches (not specifically shown).

The microcontroller 220 is further coupled to a memory 260 by a suitable data/address bus 262, wherein the programmable operating parameters used by the microcontroller 220 can be stored and modified, as required, in order to customize the operation of the device 100 to suit the needs of a particular patient. Such operating parameters define, for example, (sleep) apnea detection criteria(rion), phrenic nerve stimulation pulse amplitude(s) and frequency(ies), chest movement signals such as intrathoracic impedance signals, accelerometer signals, stimulation signal amplitude and frequency, pacing pulse amplitude, pulse duration, electrode polarity, rate, sensitivity, automatic features, arrhythmia detection criteria, etc. One feature of the described embodiments is the ability to sense and store a relatively large amount of data, which data may then be used for subsequent analysis to guide the programming of the device. The memory 260 may be used by the microcontroller 220 to load instructions and data of apnea detector 233 and PN stimulator control module 234 for execution by the microcontroller 220. Apnea detector module 233 and PN stimulator control module 234 may be initially stored in non-volatile memory (e.g., ROM, Flash, etc.) and loaded into internal memory of microcontroller and/or memory 260. The non-volatile memory is not shown but can be internal to microcontroller 220 and/or part of memory 260.

The operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 allows information relating to the operation of the device 100 (as contained in the microcontroller 220 or memory 260) and patient to be sent to the external device 254 through an established communication link 266.

The device 100 can further includes one or more physiologic sensors 270, which may be contained with the device 100 and/or outside of the device 100 (e.g., via leads that exit the device housing). For example, sensors may be used to measure chemical parameters such as tissue or blood pH, oxygen saturation, etc. A physiologic sensor commonly referred to as a "rate-responsive" sensor is optionally included and used to adjust stimulation rate and level according to the exercise state of the patient. However, one or more of the physiologic sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, diurnal changes in activity (e.g., detecting sleep and wake states), etc.

In addition to physiological sensors, the device 100 may contain other sensors such as accelerometers (not shown) which may be used to detect and monitor chest movement activity. For example, the accelerometer(s) may be used to detect the presence of apnea, e.g., in the case where no chest movement is detected for a period of time (e.g., 10 seconds).

The device 100 additionally includes a battery 276 that provides operating power to all of the circuits shown in FIG. 3. For the device 100, which may employ shocking therapy, the battery 276 is capable of operating at low current drains for long periods of time (e.g., preferably less than 10 □A), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected.

Figure 4:
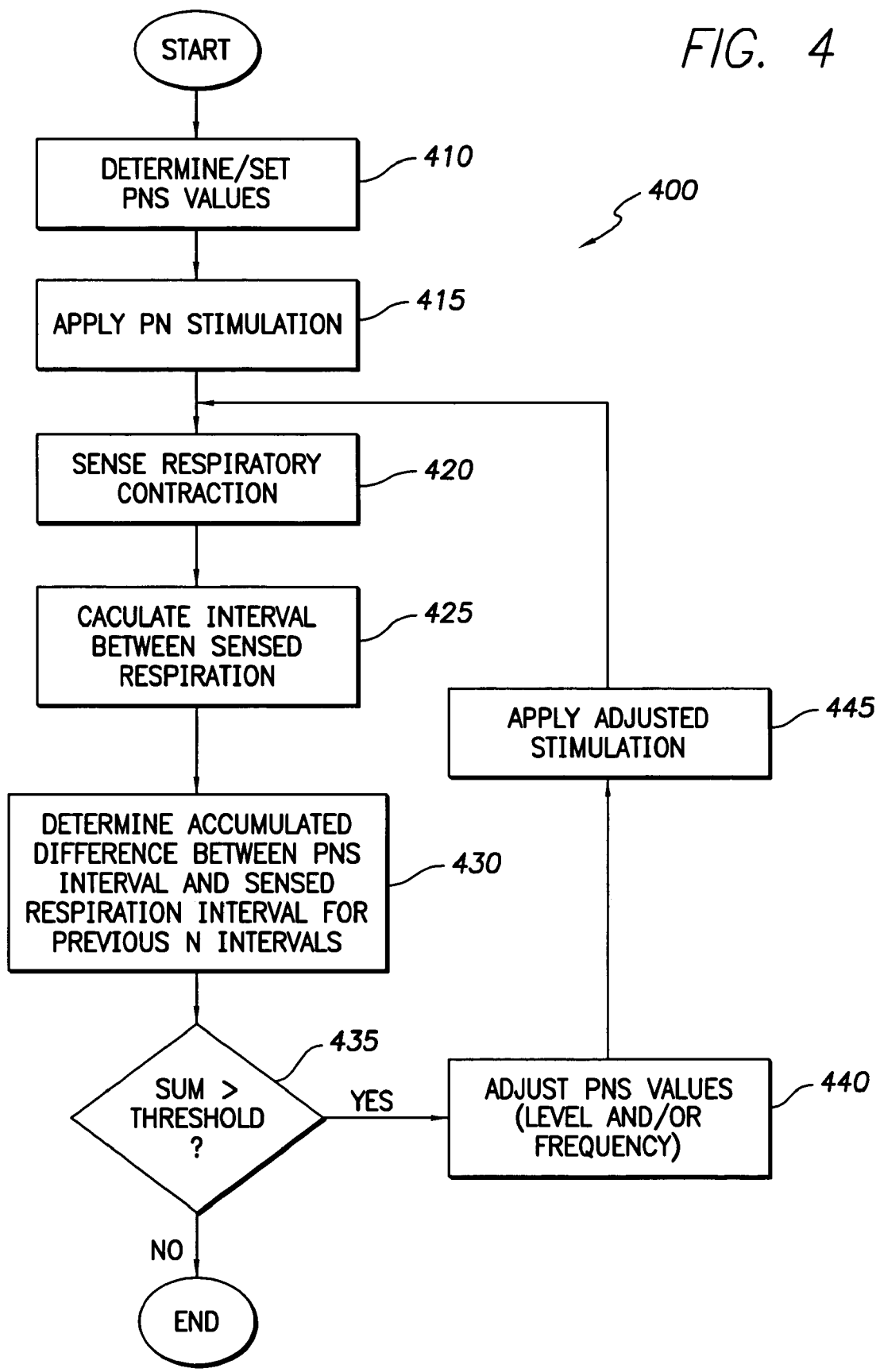
FIG. 4 is a flow diagram of an exemplary method for controlling respiration.

FIG. 4 is a block diagram of an exemplary method 400 for controlling respiration. Such an exemplary method is typically executed once a desire for inspiratory control has been determined. This would occur, for example, after apnea detector module 233 detects the presence of apnea. Apnea may be detected by monitoring the presence of (intrinsic) stimuli from the brain at the phrenic nerves 18 and 20 using sensing electrodes 144, 144" and 146, 146" and PN sensing circuit 286. If intrinsic stimuli are not detected for a predetermined time period (e.g., 10 seconds), apnea detector 233 running on microcontroller 220 will enter an apnea state to invoke PN stimulator control module 234. Respiratory information may also be inferred by sensing the person's physiological condition using sensors 270 (FIG. 3). For example, body chemistry varies in response to respiration. Hence, chemical parameters such as tissue or blood pH or blood pH as a surrogate for $PCO_2$ may be sensed and either used to infer, confirm, and/or augment other respiratory information. In addition, sensors may be used to sense oxygen saturation to make a determination of or confirm the presence of apnea. This can be accomplished using a sensor such as sensor 270. In addition, accelerometers may be used to detect or confirm the presence of apnea.

Figure 5A:
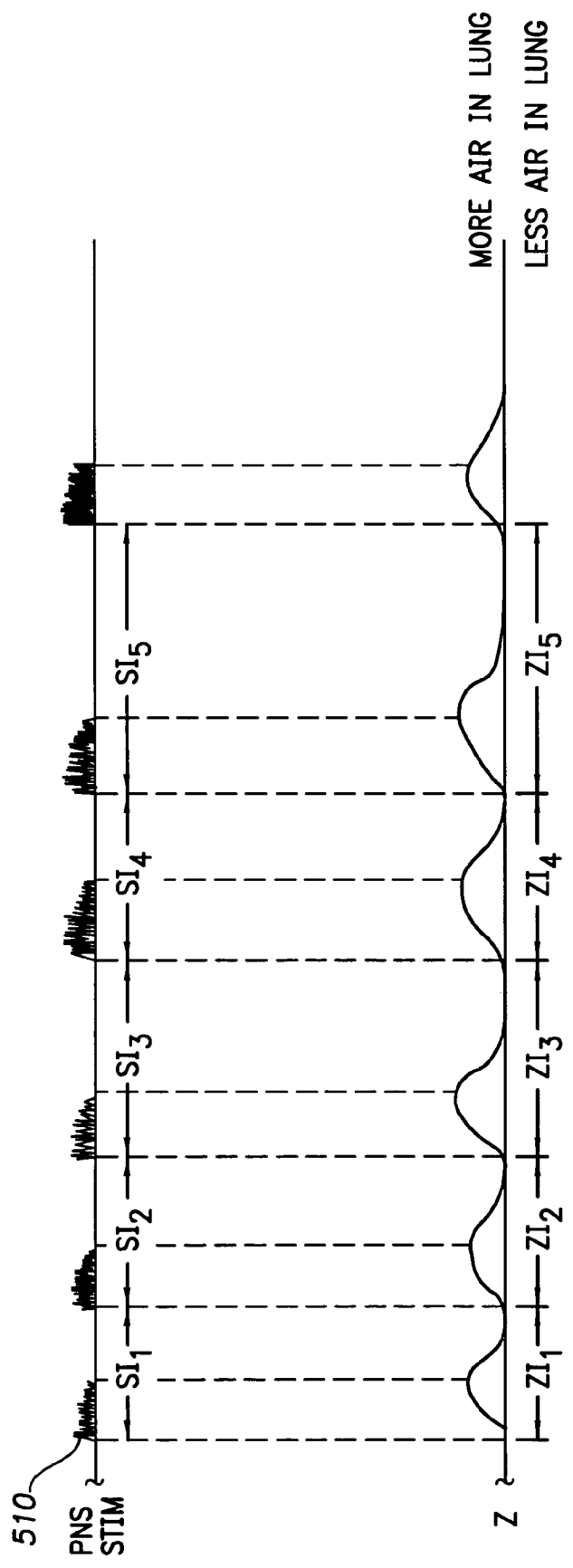
FIG. 5A shows exemplary plots of the PN stimulation signals and measured impedance over several respiration intervals, according to one embodiment of the present disclosure.

Referring to FIG. 4, once apnea is detected, the method 400 is executed. The method commences at block 410 where initial phrenic nerve stimulation values are determined and/ or set. The initial phrenic nerve stimulation values include the level, duration, and frequency of the phrenic nerve stimulation signals. The stimulation signal may have a fixed level or may vary according to a give function. The initial values may be factory default values loaded from non-volatile memory. The factory default values may be replaced with values specific to the person, including the person's CO2 level, physiological blood gas concentration, and the like. The CO2 level can be determined using a PH sensor (e.g., located in the RV or RA) while the blood gas concentration can be determined using an optical sensor (referenced as 270 in FIG. 3). Once the phrenic nerve stimulation values are determined/set, the microcontroller 220 (block 415) configures the PN stimulator 290 and switch 226 to deliver stimulation signals to the stimulation electrodes 144', 144" and 146', 146" via respective terminals 237-240. The stimulation signals may be a fixed voltage level, a varying voltage, or a series of pulses, for a specified duration. FIG. 5A (top graph) shows the PN stimulation signal 510 and PN stimulation interval $SI_i$ for each stimulation interval.

At block 420, the method senses the person's respiratory contraction. In one embodiment, respiratory contraction is sensed by measuring the intrathoracic impedance in one or more chambers in a patient's heart, which is indicative of the air volume in the lung. This can be accomplished as follows. The microcontroller 220 configures the ventricular current source 224 and switch 226 such that a constant current is applied for a predetermined duration such as for 4 microseconds between the ventricular tip electrode 128 and the can 10 (ground) via terminals 212 and 200, respectively. In one embodiment, 1 mA of constant current is applied, though this is merely exemplary. During a window immediately following the application of the constant current source, the microcontroller 220 configures the ventricular sensing circuit 246 and switch 226 to sense the voltage between the ventricular tip electrode 128 and can 10 via terminals 212 and 200, respectively. The impedance is then calculated using Ohm's law, Z=V/I. The impedance Z is calculated for a plurality of data points (e.g., 16-20 times per second) during each respiration cycle. FIG. 5A (bottom graph) shows an exemplary measured impedance plot (Z) over time. The impedance curve 515 is constructed based on the data points. The impedance interval is designated by the label $ZI_i$. It should be noted that the impedance may be measured using a different electrode located in the same or different chamber of the heart, in order to determine the air volume in the lung. The impedance may be measured using multiple electrodes. For example, the impedance can be measured using electrodes 120, 121, 122, 124, 126, 130, 132, or 134, or combinations thereof, relative to the can 10. In another embodiment, bipolar sensing may be performed to measure impedance.

Figure 5B:
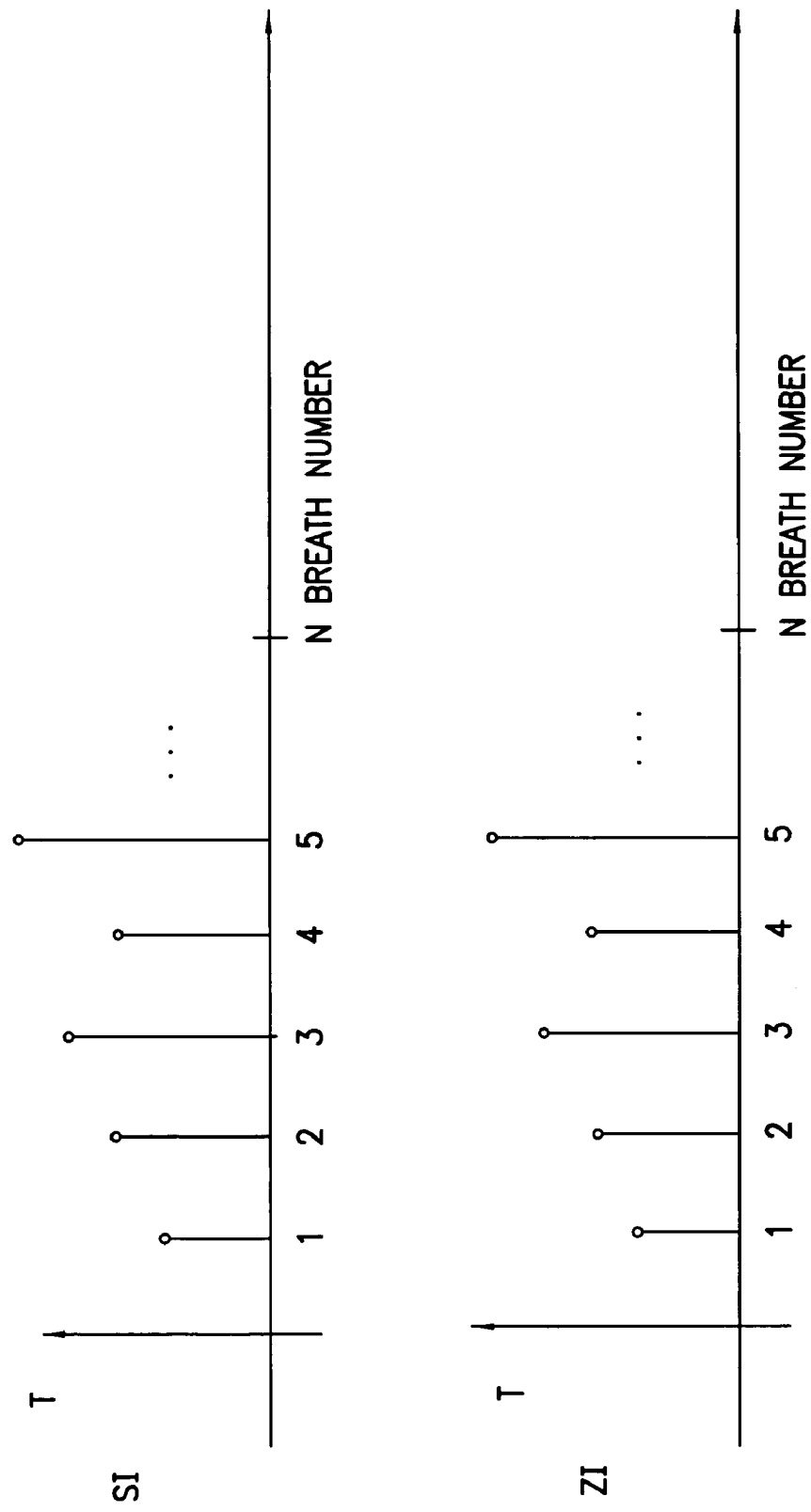
FIG. 5B shows plots of the PN stimulation interval (SI) and impedance interval (ZI) for a plurality of breaths.

The method then moves to block 425 where the impedance interval (ZI) between sensed respirations is determined. This can be determined by plotting the impedance over time and detecting when the measured impedance increases after reaching zero (or near zero). FIG. 5B (top graph) shows the duration of each stimulation interval (SI) for each breath whereas the bottom graph shows the duration of each impedance interval (ZI) for each breath. At block 430, the absolute value of the difference between the PNS interval (SI) and corresponding sensed impedance interval (ZI) is computed for each breath. The sum (SA) of the absolute value of the difference for the previous N respirations is determined, as follow:

$$SA = \Sigma_{i=1}^{N} |SI_i - ZI_i| \quad (1)$$

In equation (1), N is the number of breaths, $SI_i$ is the PN stimulation interval for breath i, $ZI_i$ is the measured impedance cycle for breath i, and SA is the accumulated difference between SI and ZI for the previous N breaths. These values are maintained in memory 260 and/or internal memory to microcontroller 220. It should be noted that N may be 1, 2, or greater. In one embodiment, N is selected such that the value of SA is accumulated for a selected time interval such as, for example, 20 seconds. A low value of SA provides a good indication that the PN stimulation signal causes a corresponding contraction. On the other hand if SA is above a predetermined threshold, this may indicate a lapse in respiratory contraction. As the frequency of these lapses increases, this is a good indication that the PN stimulation signals do not cause a corresponding contraction. As a result, higher amplitude and/or frequency PN stimulation signal may be required to obtain capture.

At block 435, SA is compared to a predetermined threshold Q. In one embodiment, the threshold Q is set between 10-20% of average measured impedance cycle for the previous N breaths. This value is set to a factory default and may be adjusted based on data measured from the person over a period of time. For instance, the difference between the intrinsic stimuli interval and sensed respiration interval of the person may be determined periodically and stored in memory. The threshold Q may be determined from this data and/or average of the data. If SA is less than the threshold Q, then the person's breathing is considered to be normal and the method ends. If SA is greater than the threshold Q, indicating that there may be a lapse in respiratory contraction, the method moves to block 440. At block 440, the amplitude and/or frequency of the PN stimulations signals are increased. In one embodiment, the amplitude and/or frequency values are adjusted based on a predetermined protocol. In one embodiment, the selection of values may be determined based on the technique(s) disclosed in co-pending U.S. patent application Ser. No. 10/938,114, filed Sep. 10, 2004, entitled "MULTI-VARIABLE FEEDBACK CONTROL OF STIMULATION FOR INSPIRATORY FACILITATION," assigned the assignee of the present invention, and incorporated fully herein by reference.

At block 445, the microcontroller 220 configures the PN stimulator 290 and switch 226 to delivery the adjusted PN stimulation signals to the stimulation electrodes 144', 144" and 146', 146" via respective terminals 237-240.

The method 400 then moves back to block 420 and executed blocks 420-445 until capture of respiratory contraction. If all amplitudes and frequencies are exhausted and contraction is not induced, the process ends. At this point, it is highly likely that a lead has failed (PNS or Z).

Figure 6:
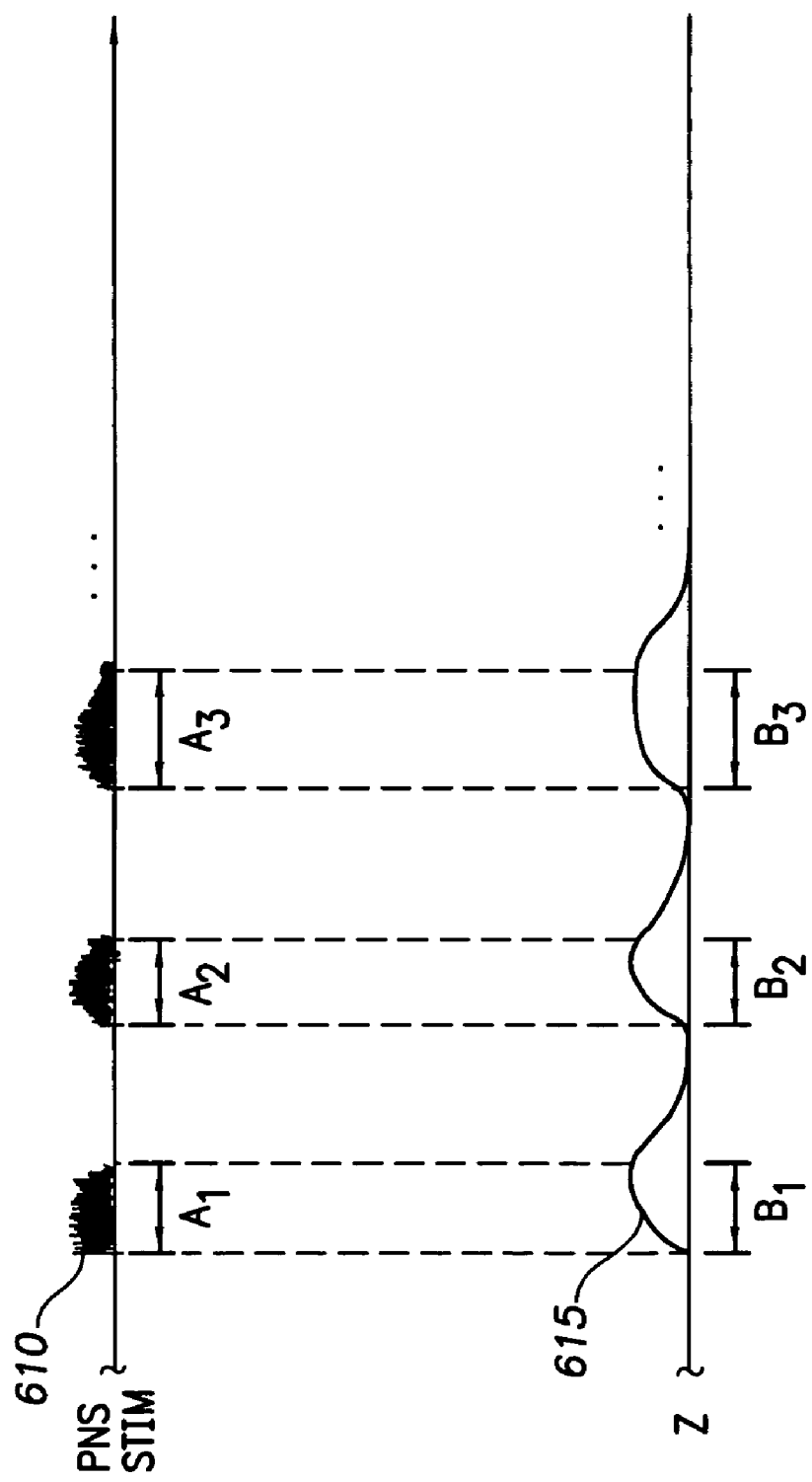
FIG. 6 shows exemplary plots of the PN stimulation signals and measured impedance over several inspiration intervals, according to one embodiment of the present disclosure.

In the embodiment described above, the PN stimulation interval (SI) and impedance interval (ZI) were based on an entire respiration cycle. In another embodiment, as shown in FIG. 6, the intervals are based only on the inspiration phase of each respiratory cycle. Thus, in the top graph of FIG. 6, 610 represents the PN stimulation signal while $A_i$ represents the duration of the PN stimulation signal 610 during the inspiration phase for each cycle. In the bottom graph of FIG. 6, 615 represents the impedance curve while $B_i$ represents the duration of the impedance curve during the inspiration phase, for each cycle. Under this embodiment, block 430 of method 400 would be modified based on the following equation:

$$SA = \sum_{i=1}^{N} |A_i - B_i| \quad (2)$$

The present invention may be implemented as a method, apparatus, system, computer program product, etc. For example, embodiments may also be directed to a microprocessor (e.g., microprocessor 220) that performs the features described herein. Additionally, an embodiment is also directed to an implantable device (e.g., device 100) that includes a microprocessor for performing such features. Further, an embodiment may also be directed to systems that perform the features discussed above. Such a system can be, for example, an external processor in communications with a microprocessor of an implantable device. When implemented in software, the elements of the present disclosure are essentially the code segments to perform the necessary tasks. The program or code segments can be stored in a processor readable medium or transmitted by a computer data signal embodied in a carrier wave over a transmission medium or communication link. The "processor readable medium" may include any medium that can store or transfer information. Examples of the processor readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, etc. The computer data signal may include any signal that can propagate over a transmission medium such as electronic network channels, optical fibers, air, electromagnetic, RF links, etc.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method, comprising:
   (a) delivering stimulation according to one or more stimulation parameters to cause contraction of a diaphragm;
   (b) monitoring chest activity related to respiration;
   (c) comparing a stimulation interval and a sensed respiration interval;
   (d) in response to comparing, adjusting one or more of the one or more stimulation parameters; and
   (e) delivering adjusted stimulation based on the one or more adjusted parameters;
   wherein (c) comprises determining an accumulation difference based on the stimulation interval and sensed respiration interval for one or more intervals.

2. The method of claim 1 wherein (a) comprises delivering stimulation to a phrenic nerve.

3. The method of claim 1 wherein (b) comprises sensing signals in a chamber of a heart.

4. The method of claim 1 wherein (b) comprises sensing signals from an accelerometer.

5. The method of claim 1 wherein the one or more stimulation parameters include one or more of the following: frequency, voltage, and pulse width.

6. The method of claim 1 wherein the stimulation interval is determined by a microcontroller executing program instructions.

7. The method of claim 1 wherein (b) comprises:
   determining the impedance level in the chamber of the heart at a plurality of times; and
   determining the respiration interval based on the impedance level at the plurality of times.

8. The method of claim 1 wherein (d) comprises adjusting one or both of a voltage level and frequency of the stimulation.

9. An implantable device to control respiration due to apnea, comprising:
   a stimulator circuit configured to couple to at least one sensor adjacent a phrenic nerve configured to generate stimulation signals to the sensor(s);

a sensing circuit configured to couple to an electrode located in a chamber of the heart and configured to receive signals;

a controller coupled to said stimulator circuit and sensing circuit and configured to:
(1) control said stimulator circuit to deliver stimulation signals according to one or more stimulation parameters to cause contraction of a diaphragm,
(2) control said sensing circuit to sense signals in the chamber of the heart,
(3) compare a stimulation interval and a sensed respiration interval,
(4) adjust one or more of the one or more stimulation parameters in response to (3), and
(5) control said stimulator circuit to deliver adjusted stimulation signals;
(6) determine an accumulation difference based on the stimulated interval and sensed respiration interval for one or more intervals.

10. The implantable cardiac device of claim 9 wherein said controller comprises a central processing unit.

11. The implantable cardiac device of claim 9 wherein said controller, as described in (1), is further configured to:
control said stimulator circuit to deliver stimulation signals to one or more phrenic nerves.

12. The implantable cardiac device of claim 9 wherein said controller, as described in (1), is further configured to:
control said stimulator circuit to deliver stimulation signals comprising at least one of a frequency, voltage, and pulse width.

13. The implantable cardiac device of claim 9 wherein said controller, as described in (2), is further configured to:

control said sensing circuit to determine an impedance level in the chamber of the heart and determine the respiration interval based on the impedance level.

14. An implantable cardiac device comprising:

means for delivering stimulation according to one or more stimulation parameters to cause contraction of the diaphragm;

means for monitoring chest activity related to respiration;

means for comparing a stimulation interval and a sensed respiration interval;

wherein the means for comparing a stimulation interval and a sensed respiration interval comprises determining an accumulation difference based on the stimulation interval and sensed respiration interval for one or more intervals; and means for determining effectiveness of the stimulation in response to the means for comparing.

15. The method of claim 14 and further comprising:

means for adjusting one or more of the one or more stimulation parameters in response to the means for determining effectiveness determining that the stimulation was not effective.

\* \* \* \* \*